PROCESS FOR PRODUCING SUBSTITUTED PYRROLES

CROSS-REFERENCE

This application is a continuation-in-part of copending application Ser. No. 209,950, filed Nov. 24, 1980, which in turn is a continuation-in-part of application Ser. No. 203,052, filed Nov. 3, 1980, both of which are now abandoned.

TECHNICAL FIELD

This invention relates to alkyl 1,4-dialkylpyrrole-2-alkanoates and derivatives thereof—more particularly to processes for preparing such esters and derivatives.

BACKGROUND

As shown in Carson's U.S. Pat. No. 3,752,826 and its divisions, U.S. Pat. Nos. 3,865,840 and 3,952,012, it is known that alkyl 1,4-dialkylpyrrole-2-alkanoates are desirable intermediates for the preparation of 5-aroylpyrrole alkanoic acids, salts, esters, nitriles, amides, and substituted amides having anti-inflammatory activity. However, a disadvantage of employing them as intermediates in the past has been the lack of a simple, economical method of making them.

The simplest of Carson's processes for preparing alkyl 1,4-dialkylpyrrole-2-alkanoates—the process taught in column 8 of U.S. Pat. No. 3,752,826—involves (1) hydrolyzing an alkyl 1,4-dialkyl-3-alkoxycarbonylpyrrole-2-alkanoate under alkaline conditions, (2) partially re-esterifying the resultant diacid to an alkyl 1,4-dialkyl-3-carboxypyrrole-2-alkanoate with an acidic solution of a lower alkanol, and (3) decarboxylating the 3-position of the resultant partial ester by heating it in an inert atmosphere until gas evolution ceases or by heating it in a suitable basic solvent, such as quinoline. When a 5-aroyl derivative is desired, the product of the decarboxylation step may be acylated with an appropriate aroyl halide under Friedel-Crafts reaction conditions, or, alternatively, the aroyl substitutent may be introduced prior to the hydrolysis step by the reactions taught by Carson in column 7.

As demonstrated in Carson's examples, specifically Examples LXXIII–LXXV, XCVIII–C, CIII–CV, CXIII–CXV, and CXXIII–CXXV, his alkyl 1,4-dialkylpyrrole-2-alkanoate syntheses are multi-step, multi-pot reactions requiring recovery of an intermediate product after each step, except when his partial esters are his starting materials. Such processes are disadvantageous, of course, because of the cost and inconvenience inherent in processes requiring more than one step and more than one reaction vessel—processes which (A) require more handling steps with attendant losses of increasingly valuable intermediates, (B) decrease positive process control, (C) increase opportunities for the introduction of impurities, (D) increase waste stream handling, (E) increase processing costs for utilities to move large amounts of intermediate materials from one reactor to another, and (F) can lead to a decrease in yield.

Moreover, even those Carson processes wherein his partial esters are his starting materials are disadvantageous. Those processes—although they have the desirable feature of being one-step processes—have the undesirable features of requiring (A) the use of considerably elevated reaction temperatures, e.g., the temperatures of 180° C. or higher that are shown in the aforementioned examples, and (B) the limitation of the starting materials to alkyl 1,4-dialkyl-3-carboxypyrrole-2-alkanoates, which, having to be synthesized from the corresponding diesters and diacids, are more expensive than the diesters and diacids that it would be desirable to be able to employ in a one-step process for preparing alkyl 1,4-dialkylpyrrole-2-alkanoates.

It is known, of course, that Carson's decarboxylation technique, i.e., heating a carboxylic material at a considerably elevated temperature under neutral conditions, is not the only means of decarboxylating a carboxylic material. Other references, such as Jones et al., *The Chemistry of Pyrroles*, Academic Press (1977), pages 327 and 329–331, show that decarboxylation of carboxylic materials, including some pyrrole acids, can be conducted under acidic, alkaline, or neutral conditions and that temperatures as low as 150° C. may be effective in some instances. However, the art does not suggest how known decarboxylation techniques could be adapted to overcome the disadvantages of Carson and make it possible to develop a generic process capable of producing alkyl 1,4-dialkylpyrrole-2-alkanoates from alkyl 1,4-dialkyl-3-alkoxycarbonylpyrrole-2-alkanoates or the corresponding diacids, dicarboxylic acid salts, ester-salts, acid-esters, or acid-salts in a single step under moderate conditions.

SUMMARY OF THE INVENTION

An object of the invention is to provide novel processes for preparing alkyl 1,4-dialkylpyrrole-2-alkanoates.

Another object is to provide such processes capable of producing alkyl 1,4-dialkylpyrrole-2-alkanoates from alkyl 1,4-dialkyl-3-alkoxycarbonylpyrrole-2-alkanoates or the corresponding diacids, dicarboxylic acid salts, ester-salts, acid-esters, or acid-salts in a single step under moderate conditions.

A further object is to provide novel processes for preparing alkyl 1,4-dialkylpyrrole-2-alkanoate derivatives, in which processes the alkyl 1,4-dialkylpyrrole-2-alkanoates are synthesized from alkyl 1,4-dialkyl-3-alkoxycarbonylpyrrole-2-alkanoates or the corresponding diacids, dicarboxylic acid salts, ester-salts, acid-esters, or acid-salts in a single step under moderate conditions.

These and other objects are attained by (A) contacting one molar proportion of a 2,3-disubstituted pyrrole corresponding to the formula:

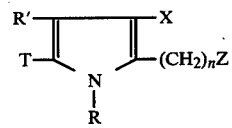

with a mixture of about 2–15 molar proportions of a strong mineral acid and amounts of an $R_1OH$ alkanol and water such as to provide an acid/alkanol mol ratio of about 0.5–6/1 and an acid/water mol ratio of about 0.3–10/1 at a temperature of about 40°–100° C. so as to form a pyrrole monoester corresponding to the formula:

is generally preferred to add the reagent mixture to the 2,3-disubstituted pyrrole, but it may sometimes be desirable to add the 2,3-disubstituted pyrrole to the reagent mixture. Also, when the reagent mixture is added to the 2,3-disubstituted pyrrole, the ingredients may be premixed or added sequentially, e.g., by adding the alkanol and then aqueous acid or by adding the alkanol, then the acid, and then the water, etc.—the only criticality being that the ingredients be added in the amounts indicated above.

The rate of reaction generally increases with an increase in temperature, and the process of the invention can be conducted at elevated temperatures as long as the temperatures are not so high as to degrade the products. However, conventional decarboxylation temperatures, e.g., about 200°-210° C., can affect the product adversely and reduce the yields substantially, while lower temperatures in the range of about 40°-100° C., preferably about 60°-85° C., have been found to be useful.

The time required for the reaction varies with the temperature employed and is not a critical variable. A small-scale reaction can be completed in less than an hour at a temperature of about 80° C., and the reaction time has varied from about 5-24 hours at 60° C. in larger-scale reactions without having any substantial adverse effect on yields.

When the reaction has been completed, the product can be recovered by extraction into an organic phase. The extraction should be conducted so as to minimize handling losses and the production of degradation by-products and, in a preferred embodiment of the invention, is conducted by (1) cooling the reaction mixture, (2) adding an organic solvent in which the pyrrole monoester is more soluble than in dilute acid, and (3) diluting with cold water while using vigorous agitation. Maintenance of a relatively low temperature during dissolution or extraction minimizes product losses from degradation of the product with the dilute acid that must be formed to permit extraction of the product with the organic solvent because of the high solubility of the pyrrole monoesters in the concentrated acid.

The solvent used for the extraction of the product can be any organic solvent in which the pyrrole monoester is more soluble than in the dilute acid. However, it is generally a chlorinated hydrocarbon or aromatic hydrocarbon, such as methylene chloride, carbon tetrachloride, chloroform, dichloroethane, benzene, toluene, xylene, monochlorobenzene, etc. When the product is to be converted to a derivative, such as a 5-aroylpyrrole anti-inflammatory agent, in a solvent, unnecessary solvent recovery and purification steps can be avoided by using as the extracting solvent a solvent that will also be useful in the subsequent reaction. Thus, toluene is a particularly preferred extractant when an anti-inflammatory agent is to be prepared from the pyrrole monoester.

When derivatives of the pyrrole monoesters, e.g., 1,4-dialkyl-5-aroylpyrrole-2-alkanoic acids, salts, amides, etc., are desired, they may be prepared by employing conventional techniques, e.g., conventional acylation, hydrolysis, ammonolysis, etc., techniques to convert the products of the present process to the desired derivatives. The particular conventional techniques used to convert the pyrrole monoesters into their various derivatives are not critical. It may sometimes be desirable to use certain particular techniques for the preparation of the derivatives, e.g., the acylation, hydrolysis, and ammonolysis techniques taught in the aforementioned Carson references, the disclosures of which are incorporated herein by reference. However, the overall processes for preparing the derivatives are simplified and made more efficient and economical by the present simplification of the synthesis of the pyrrole monoesters, regardless of the particular techniques used to convert them into their various derivatives.

The following examples are given to illustrate the invention and are not intended as a limitation thereof. In these examples certain abbreviations are used as defined below:

| Abbreviation | Definition |
| --- | --- |
| EtOH | Ethanol |
| PAT | Ethyl 1,4-dimethylpyrrole-2-acetate |
| PDE | Ethyl 1,4-dimethyl-3-ethoxycarbonylpyrrole-2-acetate |
| TMP | 1,2,4-Trimethylpyrrole |
| TMPE | 1,2,4-Trimethyl-3-ethoxycarbonylpyrrole |
| nd | none detected |
| % Yield | Yield determined by gas chromatography using an internal standard |
| % Yield* | Yield based on weight of product isolated after distillation |

EXAMPLE 1

To 50 grams of a solution of 20% ethyl 1,4-dimethyl-3-ethoxycarbonylpyrrole-2-acetate (10 grams, 40 mmoles) in toluene containing 2.4 ml of absolute ethanol (1.9 grams, 41 mmoles) were added, dropwise, over 20 minutes, 8.6 ml of 96% sulfuric acid (15 grams, 160 mmoles, containing 0.63 gram, 35 mmoles of water). During the addition, the temperature of the reaction mixture rose to about 50° C., and the mixture became heterogeneous. The reaction mixture was then heated in an oil bath at 75°-80° C. for 75 minutes with stirring. Gas evolution was observed. The reaction mixture was then diluted with 25 ml of toluene and cooled to 5° C. Then 75 ml of ice water was added in one portion with vigorous stirring. After five minutes, the organic layer was separated and dried with magnesium sulfate. Gas chromatographic analysis indicates the toluene contained 9% ethyl 1,4-dimethylpyrrole-2-acetate. The toluene was removed by vacuum distillation at 100 mm of mercury followed by vacuum distillation of the residue at 1 mm of mercury to give a fraction which weighed 5.5 grams. This corresponds to a 78% yield of ethyl 1,4-dimethylpyrrole-2-acetate.

Gas chromatographic analysis employed a Hewlett-Packard Model 5830A instrument using a 10 foot, ⅛ inch column packed with 10% DEGS on Chromosorb Q. Dibutyl phthalate was used as an internal standard and was added to the sample after work-up to avoid decomposition in the strong acid.

EXAMPLES 2-8

The purpose of this series of experiments is to illustrate the requirement for each of the components in the reagent mixture and to establish relative ratios of sulfuric acid, ethanol and water. To a number of 100 mg samples of ethyl 1,4-dimethyl-3-ethoxycarbonylpyrrole-2-acetate was added a variety of different solutions. The resultant mixtures were heated for about 18 hours at 65°-66° C. followed by pouring into 10 ml of water and extracting three times with 10 ml of methylene chloride. Each organic solution was dried with magnesium sulfate and the solvent was removed in vacuo. The residues were then heated at 190°–200° C. for 20 minutes to assure that they were entirely decarboxylated. Since all samples were treated in the same manner and the only variation was with respect to the reagent mixture added, the examples illustrate the relative importance of the components in that mixture. The composition of the reagent mixture and the results obtained as percent yield of by-products, starting materials and desired ethyl 1,4-dimethylpyrrole-2-acetate are given in the following Table 1.

TABLE 1

Reagent Mixture Composition Variability Study

| Example No. | Reagent Composition $H_2SO_4/EtOH/H_2O$ (Molar Ratio) | % Yield | | |
|---|---|---|---|---|
| | | By-Products | PAT | PDE |
| 2 | 1/0/0.22 | 21 | 3 | <1 |
| 3 | 1/0.17/0.22 | 15 | 8 | 16 |
| 4 | 1/0/0.77 | 13 | 7 | 2 |
| 5 | 1/4.8/16 | 26 | nd | 38 |
| 6 | 1/1.9/6.4 | 18 | 19 | 25 |
| 7 | 1/0.47/1.8 | 9 | 48 | nd |
| 8 | 1/0.24/0.50 | 15 | 26 | 13 |

Note that the absence of ethanol and the low amount of water in Examples 2 and 4 and the low amount of ethanol in Example 3 provide very low yields of the desired product. In contrast, when both ethanol and water are included in sufficient relative proportions as in Example 7, the yield of desired product is much higher. Further, Examples 2–8 show that the relative ratio of acid/ethanol/water is important since, if too much ethanol and water are present, the yield is substantially lower or no reaction occurs. However, as the ratio of acid to both ethanol and water increases, the yield of desired product reaches a maximum and then begins to decrease as the amount of acid exceeds by a large amount the relative amounts of ethanol and water. Note Examples 5 to 8, particularly. Therefore, the above results indicate that acid, alkanol and water are all required and that the relative proportions of each of the reagents are of great significance.

EXAMPLES 9–10

The effects of temperature and time were determined for a specified reagent mixture of sulfuric acid, ethanol and water at a molar ratio of 1/0.47/1.8, respectively, in the following Examples 9–10. Two constant temperature runs were made in which 0.5 gram of ethyl 1,4-dimethyl-3-ethoxycarbonylpyrrole-2-acetate was put into 6.7 grams (about 5 ml) of a solution consisting of 96% sulfuric acid, water, and absolute ethanol in a volume ratio of 2/1/1. The reaction mixture was heated at 60° C. in Example 9 and at 80° C. in Example 10 under a water condenser. Every hour, ½ ml of reaction mixture was worked up by pouring into 5 ml of water and extracting three times with 5 ml portions of methylene chloride. The organic layers were dried with magnesium sulfate and stripped, and the resultant residue was analyzed by gas chromatography using dibutyl phthalate as an internal standard. The results of the two examples are shown in Table 2 below.

TABLE 2

Effect of Temperature and Time on Preparation of Ethyl 1,4-Dimethylpyrrole-2-Acetate

| Example No. | Reaction Time (hr) | Percent Yield | | | |
|---|---|---|---|---|---|
| | | TMP | PAT | TMPE | PDE |
| Part A | | | | | |
| 9 | 1 | 10 | 27 | 9 | 30 |
| | 2 | 18 | 48 | 3 | 15 |
| | 3 | 22 | 59 | 1 | 7 |
| | 4 | 23 | 62 | 1 | 3 |
| | 6 | 26 | 65 | nd | nd |
| | 24 | 24 | 67 | nd | nd |
| Part B | | | | | |
| 10 | 1 | 28 | 61 | nd | nd |
| | 2 | 30 | 57 | nd | nd |
| | 3 | 30 | 58 | nd | nd |
| | 4 | 33 | 57 | nd | nd |
| | 5 | 29 | 48 | nd | nd |
| | 6 | 37 | 47 | nd | nd |
| | 72 | 26 | 28 | nd | nd |

From the table, it can be seen that the reaction time and temperature are not as critical as the reagent composition. Similar yields of the desired product, ethyl 1,4-dimethylpyrrole-2-acetate, were obtained after 3 or 4 hours at 60° C. or after 1 hour at 80°.

EXAMPLES 11–24

The following series of examples illustrates the effect of varying the pyrrole diester-treating reagent composition by using different relative amounts of acid, lower alkanol, and water. The effect on the yield of the pyrrole monoester is clearly shown.

In each example, one part by weight of ethyl 1,4-dimethyl-3-ethoxycarbonylpyrrole-2-acetate was heated with about 10.5–18.6 parts by weight of a reagent solution for one hour at a temperature of 76°–84° C. in a suitable flask provided with a water condenser and maintained in an oil bath. After the resultant reaction mixture was allowed to cool, it was poured into 10 ml of water and extracted three times with 10 ml portions of methylene chloride. The combined organic layers were dried with magnesium sulfate and concentrated in vacuo, and the residue was subjected to gas chromatographic analysis using dibutyl phthalate as the internal standard. The results of these runs are given below in Table 3.

TABLE 3

Preparation of Ethyl 1,4-Dimethylpyrrole-2-Acetate Using Variable Reagent Composition

| Example No. | Composition $H_2SO_4/EtOH*/H_2O$ (Molar Ratio) | Percent Yield | | | |
|---|---|---|---|---|---|
| | | TMP | PAT | TMPE | PDE |
| 11 | 1/0.11/0.61 | 14 | 7 | 14 | 8 |
| 12 | 1/0.19/0.89 | 13 | 15 | 15 | 20 |
| 13 | 1/0.31/1.3 | 28 | 55 | 1 | 3 |
| 14 | 1/0.47/1.8 | 24 | 61 | nd | 1 |
| 15 | 1/0.72/2.6 | 22 | 66 | nd | 2 |
| 16 | 1/1.1/3.9 | 9 | 16 | 16 | 39 |
| 17 | 1/1.9/6.4 | 1 | 1 | 18 | 55 |
| 18 | 1/0.86/0.53 | 10 | 78 | nd | 2 |
| 19 | 1/0.75/0.83 | 15 | 74 | nd | 2 |
| 20 | 1/0.67/1.2 | 14 | 64 | nd | 1 |
| 21 | 1/0.58/1.5 | 17 | 49 | 3 | 1 |
| 22 | 1/0.39/2.1 | 26 | 48 | 1 | 7 |
| 23 | 1/0.28/2.4 | 39 | 47 | nd | nd |
| 24 | 1/0.19/2.7 | 46 | 40 | nd | 1 |

For the purposes of illustration, the strong acid employed in the previous examples has been sulfuric acid.

The following examples illustrate the use of other strong acids which are illustrative of the invention.

EXAMPLE 25

To 101 mg of ethyl 1,4-dimethyl-3-ethoxycarbonyl-pyrrole-2-acetate was added 1 ml of a 1/1 volume mixture of absolute ethanol and 86% phosphoric acid. The mixture was heated in an 80° C. oil bath for 1 hour, poured into 10 ml of water, and extracted with three 10 ml portions of methylene chloride. The combined organic layers were dried (magnesium sulfate) and concentrated in vacuo to give a residue weighing 67 mg. Gas chromatographic analysis of this residue indicated it contained 33 mg (46%) of ethyl 1,4-dimethylpyrrole-2-acetate.

EXAMPLE 26

To 103 mg of ethyl 1,4-dimethyl-3-ethoxycarbonyl-pyrrole-2-acetate was added 1 ml of a solution of 1.5 ml of absolute ethanol in 5 ml of 70% perchloric acid. The mixture was heated in an 80° C. oil bath for 1 hour, poured into 10 ml of water, and extracted with three 10 ml portions of methylene chloride. The combined organic layers were dried (magnesium sulfate) and concentrated in vacuo to give a residue weighing 69 mg. Gas chromatographic analysis of this residue indicated it contained 49 mg (66%) of ethyl 1,4-dimethylpyrrole-2-acetate.

The pyrrole monoester product can be prepared from the diester neat or in the presence of a solvent. Further, while the work-up is not critical, it can have an effect on the yield of the product because of degradation of the pyrrole monoester product by dilute acid. Accordingly, the following examples illustrate preparation of the product pyrrole monoester in the presence of a solvent and show the results of work-up under conditions which do not adversely affect product yields.

EXAMPLES 27–31

A toluene solution of one molar proportion of PDE was reacted with a reagent mixture of 5 molar proportions of sulfuric acid, 1 molar proportion of ethanol, and 1.1 molar proportions of water at 80° C. for 75 minutes. The reaction mixture was then cooled to room temperature, diluted with the amount of water indicated in Table 4, and extracted with the indicated amount of toluene. The yields of PAT obtained are also indicated in the table.

TABLE 4

| | Preparation of PAT | | | |
|---|---|---|---|---|
| Example No. | Amt. of Water** | Size of Extract*** | No. of Extracts | % Yield |
| 27 | 105 | 16 | 3 | 66 |
| 28 | 117 | 16 | 4 | 62 |
| 29 | 234 | 16 | 4 | 63 |
| 30 | 134 | 11 | 4 | 74* |

**Mols of diluting water/mol PDE
***Mols of extracting solvent/mol PDE/extract

EXAMPLE 31

Example 27 was repeated except that the reaction mixture was diluted with 328 molar proportions of water and extracted with three 66 molar proportion aliquots of methylene chloride. The yield of PAT was 65%.

EXAMPLE 32

Example 31 was repeated except that neat PDE was employed instead of a toluene solution. The yield of PAT was 73%.

EXAMPLE 33

Example 28 was repeated except that neat PDE was employed instead of a toluene solution, and only three toluene extracts were made. The yield of PAT was 63%.

EXAMPLE 34

One molar proportion of PDE, employed as a 63% melt, was reacted with a reagent mixture of 5 molar proportions of sulfuric acid, one molar proportion of ethanol, and 1.1 molar proportions of water at 80° C. for 75 minutes. The reaction mixture was then divided in half. Each half of the reaction mixture was cooled, diluted with 223 molar proportions of water, and extracted with four 19 molar proportion aliquots of toluene. However, the half of the reaction mixture employed in Part A was cooled to room temperature before being diluted, and the half in Part B was cooled to 5° C. The yield* of PAT was 66% in Part A and 67% in Part B.

EXAMPLE 35

Example 34, Part A, was repeated except that the 63% PDE melt was employed as a methylene chloride solution, and the extracting solvent was methylene chloride instead of toluene. The yield* of PAT was 73%.

EXAMPLE 36

One molar proportion of neat PDE was reacted with a reagent mixture of 10 molar proportions of sulfuric acid, 10 molar proportions of ethanol, and 5 molar proportions of water at 80° C. for 75 minutes. The reaction mixture was then cooled to room temperature, diluted with 105 molar proportions of water, and extracted with four 20 molar proportion aliquots of methylene chloride. The yield* of PAT was 72%.

EXAMPLE 37

Example 36 was repeated except that the extracting solvent was toluene instead of methylene chloride. The yield of PAT was 67%.

EXAMPLE 38

Example 36 was repeated except that the reaction mixture was divided in half after dilution with water. One half was extracted with four 40 molar aliquots of methylene chloride (Part A) and the other with four 40 molar proportion aliquots of toluene (Part B). The yield of PAT was 76% in Part A and 74% in Part B.

EXAMPLE 39

One molar proportion of neat PDE was reacted with a reagent mixture of 10 molar proportions of sulfuric acid, 10 molar proportions of ethanol, and 5 molar proportions of water at 80° C. for 75 minutes. The reaction mixture was then cooled to room tempeature, diluted with 328 molar proportions of water, and extracted with three 66 molar proportion aliquots of methylene chloride. The yield of PAT was 76%.

EXAMPLE 40

Example 39 was repeated except that the amount of diluting water was 117 molar proportions, and the extraction was made with four 16 molar proportion aliquots of toluene. The yield of PAT was 64%.

EXAMPLE 41

Example 39 was repeated except that the PDE was employed as a toluene solution, the amount of diluting water was 84 molar proportions, and the extraction was made with five 5 molar proportion aliquots of toluene. The yield* was 54%.

EXAMPLE 42

One molar proportion of neat PDE was reacted with a reagent mixture of 9 molar proportions of sulfuric acid, 0.65 molar proportion of ethanol, and 2 molar proportions of water at 80° C. for 75 minutes. The reaction mixture was then cooled to room temperature, diluted with 94 molar proportions of water, and extracted with three 16 molar proportion aliquots of toluene. The yield of PAT was 15%.

EXAMPLE 43

A toluene solution of one molar proportion of PDE was reacted with a reagent mixture of 3.75 molar proportions of sulfuric acid, one molar proportion of ethanol, and 0.8 molar proportion of water at 80° C. for 75 minutes. The reaction mixture was then cooled to room temperature, diluted with 134 molar proportions of water, and extracted with four 11 molar proportion aliquots of toluene. The yield* of PAT was 67%.

EXAMPLE 44

Example 43 was repeated except that the reaction mixture was cooled to 5° C., diluted with 100 molar proportions of water, and extracted with one 16 molar proportion aliquot of toluene. The yield* of PAT was 79%.

EXAMPLE 45

To 101.5 mg of ethyl 1,4-dimethyl-3-carboxypyrrole-2-acetate were added 0.13 ml of ethanol and, dropwise, 0.13 ml of 96% sulfuric acid. The reaction mixture was then heated at 80° C. for 1 hour and 15 minutes, cooled, and poured into 2 ml of water. The diluted reaction mixture was then immediately extracted three times with 5 ml portions of methylene chloride. The combined organic layers were dried over magnesium sulfate, and the methylene chloride was removed in vacuo to give 76.5 mg of liquid. This was shown to contain, by gas chromatographic analysis using an internal standard, 75% ethyl 1,4-dimethylpyrrole-2-acetate which is a 70% yield.

EXAMPLE 46

To 99.8 mg of 1,4-dimethyl-3-ethoxycarbonylpyrrole-2-acetic acid were added 0.13 ml of ethanol and, dropwise, 0.13 ml of 96% sulfuric acid. The reaction mixture was then heated at 80° C. for 1 hour and 15 minutes, cooled, and poured into 2 ml of water. The diluted reaction mixture was then immediately extracted three times with 5 ml portions of methylene chloride, and the methylene chloride was removed in vacuo to give 76.1 mg of a liquid. This was shown to contain, by gas chromatographic analysis using an internal standard, 72% ethyl 1,4-dimethylpyrrole-2-acetate, which is a 68% yield.

EXAMPLE 47

To a mixture of 6.13 g (0.06 mole) of 96% $H_2SO_4$ and 2.07 g (0.045 mole) of ethanol, cooled to room temperature, were added 3.69 g (0.015 mole) of 80% by weight 1,4-dimethyl-3-carboxypyrrole-2-acetic acid. This provided an initial molar ratio of 1/4/0.5/3 of pyrrole reactant to acid to water to alkanol, respectively. The reaction mixture was heated with agitation at 70° C. for 3.5 hours. After 30 minutes of heating, 7.5 ml of toluene were added to aid agitation and decrease foaming caused by gas evolution. The reaction mixture was cooled to room temperature, 16 g toluene were added, and then a solution of 2.40 g of NaOH (0.06 mole) and 10.8 g $H_2O$ was slowly added at ice bath temperatures. The reaction mixture was stirred for 30 minutes, after which the organic and aqueous phases were separated. Gas chromatographic analysis of the toluene solution indicated 6.4% of ethyl 1,4-dimethylpyrrole-2-acetate, which is a 59% yield.

EXAMPLE 48

Following the procedure of Example 47, another experiment was carried out in the same manner except that 3.46 g (0.075 mols) of ethanol were employed to give a molar ratio in the initial reaction mixture of 1/4/0.5/5 of pyrrole reactant, acid, water, and alkanol, respectively. After the same heating procedure as above, followed by cooling to room temperature, toluene and caustic workup, and separation, there was obtained 25 g of the organic phase, which by gas chromatographic analysis, contained 6.6% ethyl 1,4-dimethylpyrrole-2-acetate, which is a 62% yield.

EXAMPLE 49

The procedure of Examples 47 and 48 was varied by mixing all reactants except the sulfuric acid and then adding it gradually over a period of time. To an agitated mixture of 3.46 g (0.075 mole) of ethanol, 2.90 g (0.015 mole) of 1,4-dimethyl-3-carboxypyrrole-2-acetic acid, and 7.5 g of toluene were added 6.13 g (0.06 mole) of 96% sulfuric acid, dropwise, over a period of 30 minutes. The reaction mixture was heated at 70° C. for 2 hours and then cooled to room temperature. Then 16 g of toluene were added, the reaction mixture was placed in an ice water cooling bath, and a solution of 2.4 g (0.06 mole) sodium hydroxide and 12.8 g water was added over ten minutes. The resultant mixture was stirred for 30 minutes and the organic phase, weighing 26.1 g, was separated. Based on the gas chromatographic analysis, the yield of ethyl 1,4-dimethylpyrrole-2-acetate was 80%.

EXAMPLE 50

The procedure of Example 49 was repeated except that the initial reactant mixture was heated in a 60° C. bath for 30 minutes followed by increasing the bath temperature to 80° C. and heating for an additional 1 hour and 40 minutes. Following workup, as previously described, there was obtained 26.1 g of the organic layer, which is an 84% yield of ethyl 1,4-dimethylpyrrole-2-acetate.

EXAMPLE 51

To a stirred mixture of 2.56 g (0.0117 mole) of 1,4-dimethyl-3-carboxypyrrole-2-acetate monosodium salt and 2.7 g (0.0585 mole) of ethanol in 10 g of toluene at room temperature slowly were added 4.78 g (0.0468 mole) of 96% sulfuric acid over a fifteen minute period. The initial molar ratio of pyrrole reactant to acid to water to alkanol was 1/4/0.9/5, respectively. The reaction mixture was heated for 30 minutes in a 60° C. bath and then for one hour and 15 minutes in an 80° C. bath. The reaction mixture was then cooled to room temperature, and 8.3 g of toluene were added. The reaction mixture was then placed in an ice water bath, and a solution of 1.9 g of NaOH and 8.5 g of water was slowly added. After stirring at room temperature for thirty minutes, another 2.1 g of water were added to dissolve solids which appeared. The phases were separated, and the organic phase weighed 20.2 grams. Gas chromatographic analysis showed 7.34% ethyl 1,4-dimethylpyrrole-2-acetate, which is a 70% yield. The analysis also showed 1.8% of ethyl 1,4-dimethyl-3-ethoxycarbonylpyrrole-2-acetate, which is a 13% yield.

EXAMPLE 52

The procedure of Example 51 was followed, except that the pyrrole reactant was 2.3 g (0.0095 mole) of 1,4-dimethyl-3-carboxypyrrole-2-acetic acid disodium salt. This was mixed with 2.2 g (0.0478 mole) of ethanol and 14.9 g (0.0162 mole) of toluene using stirring at room temperature. Then 5.85 g (0.0573 mole) of 96% sulfuric acid were added. The molar ratio of pyrrole reactant to acid to water to alkanol was 1/6/1.3/5, respectively. After stirring for 30 minutes upon completion of the mixing, the reaction mixture was heated in a 60° C. bath for 30 minutes and then placed in an 80° C. bath for 2 hours. The reaction mixture was then cooled with an ice water bath, and a solution of 1.55 g of NaOH and 6.9 g of water was slowly added over a fifteen minute period. The diluted reaction mixture was stirred for 30 minutes while being brought to room temperature, and the organic phase, weighing 26.4 g, was separated. Gas chromatographic analysis shows the organic phase contained 8.7% of ethyl 1,4-dimethyl-pyrrole-2-acetate and 0.64% of ethyl 1,4-dimethyl-3-ethoxycarbonylpyrrole-2-acetate, which are yields of 83% and 4.4%, respectively.

This invention is susceptible to considerable variation within the spirit and scope of the appended claims.

I claim:

1. A process which comprises contacting one molar proportion of a 2,3-disubstituted pyrrole corresponding to the formula:

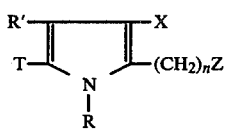

with a mixture of about 2-15 molar proportions of a strong mineral acid and amounts of an $R_1OH$ alkanol and water such as to provide an acid/alkanol mol ratio of about 0.5-6/1 and an acid/water mol ratio of about 0.3-10/1 at a temperature of about 40°-100° C., so as to form a pyrrole monoester corresponding to the formula:

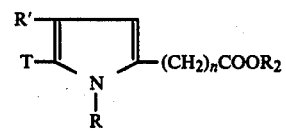

in which formulas n is an integer of 1-6; R, R', $R_1$, and $R_2$ are independently selected from lower alkyl groups; T is hydrogen or an aroyl group; and X and Z are independently selected from —COOH, —COOR$_3$, and —COOM, wherein $R_3$ is a lower alkyl group and M is sodium or potassium.

2. The process of claim 1 wherein the acid is sulfuric acid.

3. The process of claim 1 wherein n is 1.

4. The process of claim 1 wherein R and R' are methyl.

5. The process of claim 1 wherein $R_1$ and $R_2$ are ethyl.

6. The process of claim 1 wherein T is hydrogen.

7. The process of claim 1 wherein X and Z are —COOH.

8. The process of claim 1 wherein X and Z are —COOM.

9. The process of claim 1 wherein X and Z are —COOR$_3$.

10. The process of claim 9 wherein $R_3$ is ethyl.

11. The process of claim 1 wherein the 2,3-disubstituted pyrrole is dissolved in an organic solvent prior to being contacted with the acid/alkanol/water mixture.

12. The process of claim 1 wherein the contacting is effected by adding the acid/alkanol/water mixture to the 2,3-disubstituted pyrrole.

13. The process of claim 1 wherein the pyrrole monoester is recovered by diluting the reaction mixture with water, extracting the dilute solution with an organic solvent, and distilling the pyrrole monoester from the solvent.

14. The process of claim 13 wherein the solvent is methylene chloride.

15. The process of claim 13 wherein the solvent is toluene.

16. A process which comprises contacting one molar proportion of an alkyl 3-alkoxycarbonylpyrrole-2-acetate corresponding to the formula:

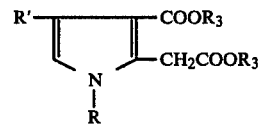

with a mixture of about 2-15 molar proportions of a strong mineral acid and amounts of an $R_1OH$ alkanol and water such as to provide an acid/alkanol mol ratio of about 0.5-6/1 and an acid/water mol ratio of about 0.3-10/1 at a temperature of about 40°-100° C., so as to form a pyrrole monoester corresponding to the formula:

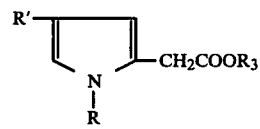

in which the formulas R, R', $R_1$, and $R_3$ are independently selected from lower alkyl groups.

17. The process of claim 16 wherein the ingredients of the reaction mixture are employed in amounts such as to provide an acid/alkyl 3-alkoxycarbonylpyrrole-2-acetate mol ratio of about 3.75–10/1, an acid/alkanol mol ratio of about 1–5/1, and an acid/water mol ratio of about 2–5/1.

18. The process of claim 16 wherein the acid is sulfuric acid.

19. The process of claim 16 wherein R and R' are methyl.

20. The process of claim 16 wherein $R_1$ and $R_3$ are ethyl.

21. The process of claim 16 wherein the alkyl 3-alkoxycarbonylpyrrole-2-acetate is dissolved in an organic solvent prior to being contacted with the acid/alkanol/water mixture.

22. The process of claim 16 wherein the contacting is effected by adding the acid/alkanol/water mixture to the alkyl 3-alkoxycarbonylpyrrole-2-acetate.

23. The process of claim 16 wherein the pyrrole monoester is recovered by diluting the reaction mixture with water, extracting the dilute solution with an organic solvent, and distilling the pyrrole monoester from the solvent.

24. The process of claim 23 wherein the solvent is methylene chloride.

25. The process of claim 23 wherein the solvent is toluene.

26. The process which comprises contacting one molar proportion of a 3-carboxypyrrole-2-acetic acid corresponding to the formula:

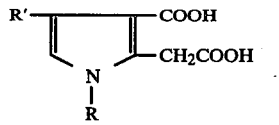

with a mixture of about 2–15 molar proportions of a strong mineral acid and amounts of an $R_1OH$ alkanol and water such as to provide an acid/alkanol mol ratio of about 0.5–6/1 and an acid/water mol ratio of about 0.3–10/1 at a temperature of about 40°–100° C., so as to form a pyrrole monoester corresponding to the formula:

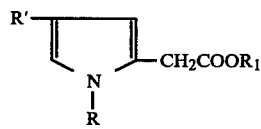

in which formulas R, R', and $R_1$ are independently selected from lower alkyl groups.

27. The process of claim 26 wherein the ingredients of the reaction mixture are employed in amounts such as to provide an acid/3-carboxypyrrole-2-acetic acid mol ratio of about 3.75–10/1, an acid/alkanol mol ratio of about 0.75–2/1, and an acid/water mol ratio of about 2–5/1.

28. The process of claim 26 wherein R and R' are methyl.

29. The process of claim 26 wherein the pyrrole monoester is recovered by diluting the reaction mixture with water, extracting the dilute solution with an organic solvent, and distilling the pyrrole monoester from the solvent.

30. The process of claim 29 wherein the solvent is toluene.

* * * * *

# United States Patent [19]

Potts

[11] 4,451,659
[45] May 29, 1984

[54] METHOD OF MAKING KNOWN AND PREVIOUSLY UNAVAILABLE PYRYLIUM SALTS

[75] Inventor: Kevin T. Potts, Schenectady, N.Y.

[73] Assignee: Rensselaer Polytechnic Institute, Troy, N.Y.

[21] Appl. No.: 364,893

[22] Filed: Apr. 2, 1982

[51] Int. Cl.$^3$ .................... C07D 309/32; C07F 5/02
[52] U.S. Cl. ................................. 549/4; 260/239 R; 546/256; 546/268; 549/28; 549/416; 549/417
[58] Field of Search .............. 260/239 R; 549/4, 28, 549/416, 417; 546/256, 268

[56] References Cited

U.S. PATENT DOCUMENTS 4,343,948  8/1982  Kawamura et al. ............ 549/416 X

FOREIGN PATENT DOCUMENTS 3011279  10/1980  Fed. Rep. of Germany .

Primary Examiner—Richard Raymond
Attorney, Agent, or Firm—McGlew and Tuttle

[57] ABSTRACT

A method is disclosed for preparing pyrylium and thiapyrylium salts having the formula represented below (where X is O, S or Se):

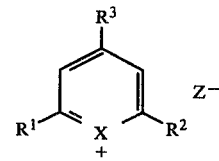

and where $R^1$ and $R^2$ represents a branched or unbranched alkyl radical having up to about 15 carbon atoms, an aromatic group having as substituents alkyl radicals with 1 to about 15 carbon atoms, alkoxy radicals having 1 to about 4 carbon atoms, substituted amino radicals have 1 to 2 carbon radicals containing 1 to about 4 carbon atoms, a heterocyclic group having as substitute alkyl radicals with 1 to about 15 carbon atoms, alkoxy radicals having 1 to about 4 carbon atoms and amino radicals having 1 or 2 carbon radicals containing 1 to about 4 carbons, thiophene radicals and furan radical containing a variety of substituents; $R^3$ represents a thioalkyl radical having 1 to about 4 carbon atoms thiobenzyl, thioaryl and thiocycloalkyl, as well as thiohetaryl radicals such as thiohydridyl and related 5- and 6-membered systems; and $Z^-$ is an anionic function. The salts are prepared by condensing the methyl ketone with carbon disulfide in the presence of sodium hydride, treating the product with methyl iodide to form the α-oxoketenedithioacetal; condensing the α-oxoketenedithioacetal with another methyl ketone in the presence of two equivalents of potassium tert-butoxide to form a 1,5-enedione; and cyclizing the enedione with tetrafluoroboric acid.

11 Claims, No Drawings